US006989459B2

(12) United States Patent
Walker

(10) Patent No.: US 6,989,459 B2
(45) Date of Patent: Jan. 24, 2006

(54) IN SITU PROCESS FOR PREPARING QUATERNARY AMMONIUM BICARBONATES AND QUATERNARY AMMONIUM CARBONATES

(75) Inventor: Leigh E. Walker, Macungie, PA (US)

(73) Assignee: Lonza Inc., Fair Lawn, NJ (US)

( * ) Notice: Subject to any disclaimer, the term of this patent is extended or adjusted under 35 U.S.C. 154(b) by 87 days.

(21) Appl. No.: 10/776,368

(22) Filed: Feb. 10, 2004

(65) Prior Publication Data

US 2004/0162343 A1 Aug. 19, 2004

Related U.S. Application Data

(62) Division of application No. 10/188,692, filed on Jul. 2, 2002, now Pat. No. 6,784,307.
(60) Provisional application No. 60/303,971, filed on Jul. 9, 2001.

(51) Int. Cl.
C07C 69/96 (2006.01)

(52) U.S. Cl. .................. 558/277; 558/260; 558/276
(58) Field of Classification Search ................ 558/276, 558/277, 260
See application file for complete search history.

(56) References Cited

U.S. PATENT DOCUMENTS

| 2,635,100 | A | 4/1953 | Werntz et al. ............... 260/244 |
| 3,642,858 | A | 2/1972 | Frevel et al. ............... 260/463 |
| 3,803,201 | A | 4/1974 | Gilpin et al. ............... 260/463 |
| 4,062,884 | A | 12/1977 | Romano et al. ............ 260/462 |
| 4,181,676 | A | 1/1980 | Buysch et al. ............... 260/463 |
| 4,572,769 | A | 2/1986 | Shimizu .................... 204/59 R |
| 4,634,509 | A | 1/1987 | Shimizu et al. ........... 204/182.4 |
| 4,652,667 | A | 3/1987 | Green ........................ 558/277 |
| 4,661,609 | A | 4/1987 | Knifton ...................... 558/277 |
| 4,691,041 | A | 9/1987 | Duranleau et al. .......... 558/277 |
| 4,734,518 | A | 3/1988 | Knifton ...................... 558/277 |
| 4,776,929 | A | 10/1988 | Aoyami et al. ............ 204/59 R |
| 4,892,944 | A | 1/1990 | Mori et al. ................. 544/107 |
| 5,091,543 | A | 2/1992 | Grey .......................... 549/228 |
| 5,214,182 | A | 5/1993 | Knifton ...................... 558/277 |
| 5,438,034 | A | 8/1995 | Walker ....................... 504/158 |
| 5,523,487 | A | 6/1996 | Walker ....................... 564/296 |
| 5,833,741 | A | 11/1998 | Walker ......................... 106/2 |
| 6,080,789 | A | 6/2000 | Lutz ........................... 514/642 |

FOREIGN PATENT DOCUMENTS

EP 0291074 11/1988

OTHER PUBLICATIONS

Chemical Abstract 108:194813.
Chemical Abstract 109:140942c.
Chemical Abstract 144:246824j.
Chemical Abstract 116:58737a.
Chemical Abstract 116:20680p.
Chemical Abstract 117:191329f.
Chemical Abstract 118:168685f.
Chemical Abstract 112:186941y.
Chemical Abstract 123:9063p.
Chemical Abstract 116:83918t.
Chemical Abstract 108:195813j.
Chemical Abstract 109:200000f.
Chemical Abstract 110:212114e.
Chemical Abstract 112:9801h.
Chemical Abstract 122:186906r
Chemical Abstract 125:186942z.
Chemical Abstract 114:246809h.
Chemical Abstract 115:282480y.
Chemical Abstract 117:214936t.
Chemical Abstract 117:111138e.
Chemical Abstract 119:138758k.
Chemical Abstract 119:141608s.
Chemical Abstract 118:254406x.
Chemical Abstract 115:282446s.
Chemical Abstract 121:230349s.
Chemical Abstract 117:193966k.
Chemical Abstract 116:237798t.
Chemical Abstract 116:193723h.
Chemical Abstract 112:258494j.
Chemical Abstract 121:38041u.
Chemical Abstract 121:179111d.
Chemical Abstract 121:133543t.
Chemical Abstract 114:246810b.
Chemical Abstract 95:6499c.
Chemical Abstract 122:160111c.
Chemical Abstract 122:160112d.
Chemical Abstract 122:217155b, and 122:217155c.
Chemical Abstract 118:80498m.
Chemical Abstract 111:23523x.
Chemical Abstract 122:132593t.

(Continued)

Primary Examiner—Golam M M Shameem
(74) Attorney, Agent, or Firm—Darby & Darby

(57) ABSTRACT

Applicant has discovered an in situ method of preparing quaternary ammonium methocarbonate salts and quaternary ammonium alkylcarbonate salts in high yield from tertiary amines, methanol, and at least one of a cyclic carbonate, an aliphatic polyester (such as a polycarbonate), or an ester (such as a carbonate ester), and their subsequent conversion to quaternary ammonium bicarbonates, quaternary ammonium carbonates or both in a one-pot reaction. According to one embodiment of the invention, the method includes reacting an amine and methanol with at least one of a cyclic carbonate and an aliphatic polyester to yield a quaternary ammonium methocarbonate. This method does not produce or require the handling of corrosive quaternary ammonium hydroxides. Another embodiment is a method of preparing quaternary ammonium alkylcarbonate salts by reacting tertiary amines, methanol, and an ester. The quaternary ammonium methocarbonate or alkylcarbonate can be converted to the corresponding bicarbonate, carbonate, or mixture thereof by methods known in the art.

12 Claims, No Drawings

OTHER PUBLICATIONS

"Reactions of Trihalogenated Esters with Triethylamine and Anions", Arlene C. Pierce and Madeleine M. Joullie, *J. Org. Chem.* vol. 27, pp. 3968–3973 (1962).

"Industrial Organic Nitrogen Compounds", ASTLE . . . Ed; Reinhold Pub. (1961), p. 61.

"Reaction of Xanthates with *t*–Amines, VI. The Reaction Mechanism", Hiroshi Yoshida, *Bull. of Chem. Soc. of JP,* vol. 42, p. 1948–1954 (1969).

"Zur solvensfreien Darstellung von Tetramethylammonium-salzen: Synthese und Charakterisierung von et al.", B. Altert und M. Jansen, *Z. Anorg. Allg. Chem.* 621, p. 1735–1740 (1995).

"The Rate of Addition of Methyl Esters to Trimethylamine", *JACS* 55:4079–4089 (Oct. 1933).

Yagi, O. et al.: "Synthesis of pure tetramethylammonium hydroxide solution free from chloride ion by the electrolysis of its hydrogen carbonate" Chemistry Letters, vol. 12, 1993, pp. 2041–2044, XP002218995 p. 2042; table 1.

Database WPI, Section Ch, Week 199141, Derwent Publications Ltd., London, GB; AN 1991–298749; XP002218996 & JP 03 197449 A (Mitsui Petrochem Ind Co Ltd), Aug. 28, 1991, abstract.

Database WPI, Section Ch, Week 199517, Derwent Publications Ltd., London, GB; AN 1995–128295, XP002218997 & JP 07 053478 A (Mitsubishi Gas Chem Co Inc), Feb. 28, 1995, abstract.

Int'l Search Report mailed Nov. 27, 2002 for Int's Application No. PCT/US 02/21236.

IN SITU PROCESS FOR PREPARING QUATERNARY AMMONIUM BICARBONATES AND QUATERNARY AMMONIUM CARBONATES

This application is a divisional of U.S. Ser. No. 10/188,692, filed Jul. 2, 2002, now U.S. Pat. No. 6,784,307, which claims the benefit of U.S. Provisional Application No. 60/303,971, filed Jul. 9, 2001, which is hereby incorporated by reference.

FIELD OF THE INVENTION

This invention relates to an in situ method of preparing quaternary ammonium alkylcarbonates (such as quaternary ammonium methocarbonates), quaternary ammonium bicarbonates, and quaternary ammonium carbonates from corresponding tertiary amines.

BACKGROUND OF THE INVENTION

Quaternary ammonium compounds, such as didecyldimethyl ammonium carbonate and didecyldimethyl ammonium chloride, are known to have antimicrobial activity. See, for example, U.S. Pat. Nos. 5,523,487, 5,833,741, and 6,080,789. Quaternary ammonium compounds have been found to be particularly useful as wood preservatives. However, quaternary ammonium chloride have been found to leach rapidly in soil (Nicholas et al., Forest Prod. J., 41:41 (1991)). Consequently, a metal coupler, such as a copper salt, is frequently added to the quaternary ammonium chlorides to prevent leaching.

Quaternary ammonium carbonates, on the other hand, have better leaching resistance and do not require the use of a metal coupler. As a result, there is an increasing demand in the preservative market for quaternary ammonium carbonates.

U.S. Pat. No. 5,438,034 discloses a process for preparing quaternary ammonium carbonates. The process includes reacting a quaternary ammonium chloride with a metal hydroxide to form a quaternary ammonium hydroxide and then reacting the quaternary ammonium hydroxide with carbon dioxide to yield the quaternary ammonium carbonate. The quaternary ammonium hydroxide, however, is very corrosive. In addition, metal chloride produced as a byproduct in the first reaction must be filtered out of the reaction product, a step which increases the cost and decreases the efficiency of the process. Thus, an alternative method to produce quaternary ammonium carbonates is desirable.

Werntz, U.S. Pat. No. 2,635,100, discloses a process for preparing quaternary ammonium carbonates by reacting a trialiphatic amine with a dialiphatic hydrocarbon ester of carbonic acid, such as dimethyl carbonate and ethylene carbonate, preferably in the presence of an alcohol. Werntz reported that the reaction of tertiary amines and dimethyl carbonate yielded quaternary ammonium methocarbonates. Werntz also reported that when ethylene carbonate was reacted with triethylamine and methanol, the cyclic carbonate of triethyl-2-hydroxyethylammonium hydroxide was formed. The solvent, unreacted amine, and cyclic ester were removed by distillation. Many dialiphatic hydrocarbon esters of carbonic acid, such as dimethyl carbonate, are expensive and, therefore, significantly increase the cost of preparing quaternary ammonium carbonates by this process.

Dimethyl carbonate is commercially available, and methods of its synthesis are well known in the art. Typically cyclic carbonates, e.g., ethylene and propylene carbonate, are converted to dimethyl carbonate and a glycol in the presence of methanol or other alcohol and catalyst. Romano et al., U.S. Pat. No. 4,062,884, disclose a process for preparing dialkylcarbonates by reacting an alcohol with a cyclic carbonate in the presence of an organic base, such as a tertiary aliphatic amine. Romano et al. describe the reaction of a methanol/ethylene carbonate/triethylamine mixture. Continuous distillation of the methanol-dimethylcarbonate azeotrope over 3 hours resulted in almost complete conversion of ethylene carbonate to ethylene glycol and dimethyl carbonate. Romano et al. further teach that the organic base which catalyzes the reaction can be totally recovered from the reaction vessel by simple distillation.

There is a continuing need for cheaper and more efficient methods for preparing quaternary ammonium carbonates. A one step, in situ method of preparing quaternary ammonium carbonates would advantageously meet these needs.

SUMMARY OF THE INVENTION

Applicant has discovered an in situ method of preparing quaternary ammonium methocarbonate salts and quaternary ammonium alkylcarbonate salts in high yield from tertiary amines, methanol, and at least one of a cyclic carbonate, an aliphatic polyester, and an ester, and their subsequent conversion to quaternary ammonium bicarbonates, quaternary ammonium carbonates or both in a one-pot reaction. According to one embodiment of the invention, the method includes reacting an amine and methanol with at least one of a cyclic carbonate, an aliphatic polyester (such as a polycarbonate), or an ester (such as a carbonate ester) to yield a quaternary ammonium methocarbonate. This method does not produce or require the handling of corrosive quaternary ammonium hydroxides. Furthermore, this method advantageously produces glycols as byproducts. Glycols are frequently added to solutions containing quaternary ammonium carbonates and quaternary ammonium bicarbonates to raise their flashpoint and as an anti-freeze.

Another embodiment is a method of preparing quaternary ammonium alkylcarbonate salts by reacting tertiary amines, methanol, and an ester.

The present invention also provides a method of preparing a quaternary ammonium bicarbonate, quaternary ammonium carbonate, or mixture thereof by (a) preparing a quaternary ammonium methocarbonate or a quaternary ammonium alkylcarbonate by one of the aforementioned methods, and (b) converting the quaternary ammonium methocarbonate or quaternary ammonium alkylcarbonate to the corresponding quaternary ammonium bicarbonate, quaternary ammonium carbonate, or mixture thereof.

DETAILED DESCRIPTION OF THE INVENTION

Applicant has discovered an in situ method of preparing quaternary ammonium methocarbonate and alkylcarbonate salts in high yield from tertiary amines, methanol, and at least one of a cyclic carbonate, an aliphatic polyester (such as a polycarbonate), and/or an ester (such as a carbonate ester), and their subsequent conversion to quaternary ammonium bicarbonates, quaternary ammonium carbonates, or mixtures thereof in a one-pot reaction.

The term "alkyl" as used herein includes straight and branched alkyl substituents. An "alkyl" group is a saturated hydrocarbon.

Preparation of the Quaternary Ammonium Methocarbonate

The method of the present invention can prepare quaternary ammonium methocarbonates having the formula

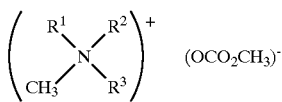

where $R^1$, $R^2$, and $R^3$ are independently $C_1$–$C_{30}$ alkyl. Preferably, $R^1$, $R^2$, and $R^3$ are independently $C_1$–$C_{20}$ alkyl and more preferably are independently $C_1$–$C_{16}$ alkyl. Most preferably, $R^1$ is methyl.

Also, at least one of $R^1$, $R^2$, and $R^3$ is preferably a $C_8$–$C_{30}$ alkyl or a $C_8$–$C_{20}$ alkyl. According to one embodiment, $R^1$ and $R^2$ are independently $C_1$–$C_{20}$ alkyl and more preferably are independently $C_1$–$C_{16}$ alkyl and $R^3$ is $C_8$–$C_{20}$ alkyl and more preferably $C_8$–$C_{16}$ alkyl.

According to a preferred embodiment, $R^2$ is $C_1$–$C_{20}$ alkyl. According to another embodiment, $R^2$ is methyl. According to yet another embodiment, $R^2$ is a $C_8$–$C_{12}$ alkyl and more preferably a $C_{10}$ alkyl.

According to a preferred embodiment, $R^3$ is a $C_8$–$C_{12}$ alkyl and more preferably a $C_{10}$ alkyl.

According to another preferred embodiment, $R^1$ is methyl and $R^2$ and $R^3$ are independently $C_8$–$C_{20}$ alkyl. More preferably, $R^2$ and $R^3$ are independently $C_8$–$C_{12}$ alkyl. According to a more preferred embodiment, $R^2$ and $R^3$ are $C_{10}$ alkyl.

According to yet another preferred embodiment, $R^1$ and $R^2$ are methyl and $R^3$ is a $C_8$–$C_{20}$ alkyl. According to one embodiment, $R^3$ is a $C_{10}$–$C_{18}$ alkyl and more preferably is a $C_{12}$ or $C_{18}$ alkyl. According to another embodiment, $R^3$ is $C_8$–$C_{12}$ alkyl and more preferably is a $C_{10}$ alkyl.

Representative quaternary ammonium methocarbonates include, but are not limited to, didecyldimethyl ammonium methocarbonate, dodecyltrimethyl ammonium methocarbonate, dioctyldimethyl ammonium methocarbonate, octadecyltrimethyl ammonium methocarbonate, dioctadecyldimethyl ammonium methocarbonate, trioctylmethyl ammonium methocarbonate, and any combination of any of the foregoing.

The quaternary ammonium methocarbonate is prepared by reacting an amine and methanol with at least one of a cyclic carbonate, an aliphatic polyester (such as a polycarbonate), or an ester (such as a carbonate ester). Suitable amines include, but are not limited to, those having the formula $NR^1R^2R^3$, wherein $R^1$, $R^2$, and $R^3$ are defined as above. Preferred amines include, but are not limited to, didecylmethylamine, dodecylmethylamine, dioctylmethylamine, octadecyldimethylamine, dioctadecylmethylamine, trioctylamine, and any combination of any of the foregoing.

Suitable cyclic carbonates include, but are not limited to, those having the formula

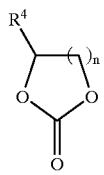

where $R^4$ is hydrogen or $C_1$–$C_4$ alkyl and n is an integer from 1 to 10. Preferably, $R^4$ is hydrogen or methyl. Preferred cyclic carbonates include, but are not limited to, ethylene carbonate, propylene carbonate, and mixtures thereof.

Suitable aliphatic polyester include, but are not limited to, those having the formula

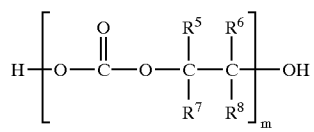

where $R^5$, $R^6$, $R^7$, and $R^8$ are independently hydrogen or $C_1$–$C_{10}$ alkyl and m is an integer from 1 to 1200. According to one embodiment, $R^5$, $R^6$, $R^7$, and $R^8$ are independently hydrogen or $C_1$–$C_4$ alkyl. Preferably, $R^5$, $R^6$, $R^7$, and $R^8$ are independently hydrogen or methyl. According to a preferred embodiment, $R^5$ is methyl and $R^6$, $R^7$, and $R^8$ are hydrogen. Preferably, m ranges from 1 to 100.

Generally, the reaction is performed with a molar excess of methanol and cyclic carbonate, aliphatic polyester, or mixture thereof with respect to amine, i.e., the molar ratios of methanol and the cyclic carbonate, aliphatic polyester, or mixture thereof to amine are greater than 1. The molar ratio of amine to cyclic carbonate, aliphatic polyester, or mixture thereof preferably ranges from about 1:1 to about 1:10 and more preferably ranges from about 1:1.1 to about 1:1.3. The molar ratio of amine to methanol broadly ranges from about 1:2 to about 1:20 and preferably ranges from about 1:3 to about 1:10.

The reaction is typically performed at from about 120 to about 160° C., preferably from about 120 to about 150° C., and more preferably from about 120 to about 140° C. The reaction may be performed at a pressure ranging from about 60 to about 200 psi. Preferably, the reaction is performed at a pressure ranging from about 120 to about 150 psi.

Generally, the reaction is performed for from about 3 to about 40 hours and preferably from about 5 to 30 hours.

The reaction step yielding the quaternary ammonium methocarbonate also produces glycols, such as ethylene glycol and propylene glycol, as byproducts. For example, when the cyclic carbonate is propylene carbonate, the reaction is as follows:

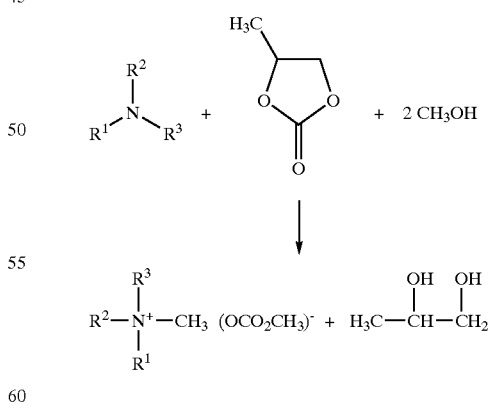

where $R^1$, $R^2$, and $R^3$ are defined as above.

Without being bound by any theory, the inventor believes that the propylene carbonate first reacts with methanol to form dimethyl carbonate and propylene glycol as shown below.

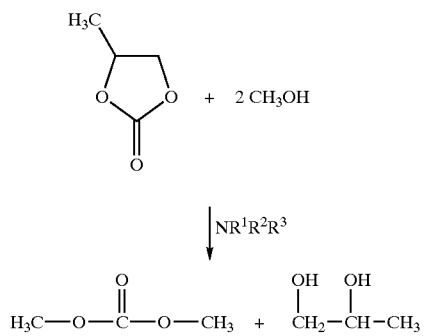

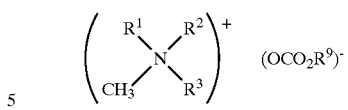

The amine $NR^1R^2R^3$ catalyzes this first reaction. The inventor further hypothesizes that the dimethyl carbonate formed reacts with the amine to yield the quaternary ammonium methocarbonate. Therefore, the reaction yields quaternary ammonium methocarbonate and propylene glycol.

Dimethyl carbonate may also be added to the reaction mixture to improve the kinetics of the reaction, i.e., to accelerate the reaction. The dimethyl carbonate also functions to balance the ratio of quaternary ammonium bicarbonate and carbonate to glycol in the product. The molar ratio of amine to dimethyl carbonate (before the reaction) preferably ranges from about 2:1 to about 1:3 and more preferably ranges from about 1.25:1 to about 1:1.25.

The inventor has found that the molar ratio of total carbonate sources (i.e. total cyclic carbonate and aliphatic polyester) to amine in the reaction is preferably in the range of from about 1:1 to 5:1, more preferably 1.25:1 to 2.5:1, and most preferably 1:1.5 to 1:2.

Thus, the present reaction in a preferred embodiment uses a molar excess of methanol and dimethyl carbonate relative to amine to substantially completely convert the amine to quaternary ammonium methocarbonate. The cyclic carbonate is preferably substantially completely converted to glycol and dimethyl carbonate. The glycol can remain in the product.

The molar ratio of cyclic carbonate to amine can be varied to obtain the desired weight ratio of glycol to quaternary ammonium methocarbonate in the reaction product. While methanol in the final product can be easily distilled off, removal of glycols is much more costly. According to one embodiment, the molar ratio of cyclic carbonate to amine is slightly greater than 1, e.g., from about 1:1.1 to about 1:1.5 or from about 1:1.1 to about 1:1.3. By keeping the molar ratio near 1, the weight ratio of propylene glycol to quaternary ammonium methocarbonate, such as didecyldimethyl ammonium methocarbonate, in the final product generally ranges from about 1:3 to about 1:7 and is preferably about 1:5.

After the formation of the quaternary ammonium methocarbonate, excess methanol and dimethyl carbonate may be removed and recovered by simple distillation. The quaternary ammonium, methocarbonate may be isolated and purified by methods known in the art.

Preparation of the Quaternary Ammonium Alkylcarbonate

According to another embodiment of the present invention, quaternary ammonium alkylcarbonates having the formula where $R^1$, $R^2$, and $R^3$ are defined as above and $R^9$ is a $C_1$–$C_{10}$ alkyl. According to one preferred embodiment, $R^9$ is a $C_1$–$C_4$ alkyl. More preferably, $R^9$ is methyl, ethyl, or propyl.

Representative quaternary ammonium alkylcarbonates include, but are not limited to, didecyldimethyl ammonium ethylcarbonate, dodecyltrimethyl ammonium ethylcarbonate, dioctyldimethyl ammonium ethylcarbonate, octadecyltrimethyl ammonium ethylcarbonate, dioctadecyldimethyl ammonium ethylcarbonate, trioctylmethyl ammonium ethylcarbonate, and any combination of any of the foregoing.

The quaternary ammonium alkylcarbonate is prepared by reacting an amine and methanol with an ester. Suitable amines include, but are not limited to, those described above.

Suitable esters include, but are not limited to, those having the formula

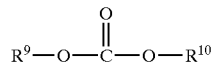

wherein $R^9$ is defined as above and $R^{10}$ is a $C_1$–$C_{10}$ alkyl. According to one embodiment, $R^{10}$ is a $C_1$–$C_4$ alkyl, such as methyl, ethyl, or propyl. A preferred ester is diethyl carbonate (i.e. where $R^9$ and $R^{10}$ are ethyl)

Generally, the reaction is performed with a molar excess of methanol and ester with respect to amine, i.e., the molar ratios of methanol and ester to amine are greater than 1. The molar ratio of amine to ester preferably ranges from about 1:1 to about 1:10 and more preferably ranges from about 1:1.1 to about 1:1.3. The molar ratio of amine to methanol broadly ranges from about 1:2 to about 1:20 and preferably ranges from about 1:3 to about 1:10.

The reaction conditions are generally the same as those described for the preparation of the methocarbonate.

The reaction step yielding the quaternary ammonium alkylcarbonate also produces alkanols having the formula $R^9OH$, $R^{10}OH$, or mixtures thereof. For example, when the ester is cyclic carbonate is propylene carbonate, the reaction is as follows:

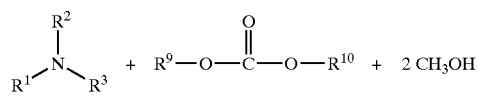

-continued

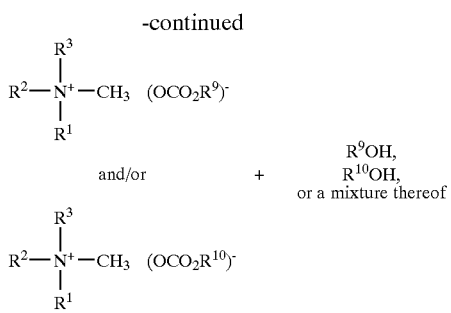

where $R^1$, $R^2$, $R^3$, $R^9$, and $R^{10}$ are defined as above.

Without being bound by any theory, the inventor believes that the ester first reacts with methanol to form a methyl ester of the formula $CH_3OC(O)OR^9$, $CH_3OC(O)OR^{10}$, or a mixture thereof and $R^9OH$, $R^{10}OH$, or a mixture thereof. The amine $NR^1R^2R^3$ catalyzes this first reaction. The inventor further hypothesizes that the methyl ester formed reacts with the amine to yield the quaternary ammonium alkylcarbonate. Therefore, the reaction yields quaternary ammonium alkylcarbonate and alkanol ($R^9OH$, $R^{10}OH$, or a mixture thereof). The alkylcarbonate anion of the quaternary ammonium alkyl carbonate can be $[OC(O)OR^9]^-$, $[OC(O)OR^{10}]^-$, or a mixture thereof.

Alkyl methyl carbonate of the formula of the formula $R^9OC(O)OCH_3$ or $R^{10}OC(O)OCH_3$ may also be added to the reaction mixture to improve the kinetics of the reaction, i.e., to accelerate the reaction. The molar ratio of amine to alkyl methyl carbonate (before the reaction) preferably ranges from about 2:1 to about 1:3 and more preferably ranges from about 1.25:1 to about 1:1.25.

The inventor has found that the molar ratio of total carbonate sources (i.e. total ester) to amine in the reaction is preferably in the range of from about 1:1 to 5:1, more preferably 1.25:1 to 2.5:1, and most preferably 1:1.5 to 1:2.

Thus, the present reaction in a preferred embodiment uses a molar excess of methanol and alkyl methyl carbonate relative to amine to substantially completely convert the amine to quaternary ammonium alkylcarbonate. The ester is substantially completely converted to alkanol and alkyl methyl carbonate. The alkanol remains in the product.

After the formation of the quaternary ammonium alkylcarbonate, excess methanol and alkyl methyl carbonate may be removed and recovered by simple distillation. The quaternary ammonium alkylcarbonate may be isolated and purified by methods known in the art.

Conversion of the Quaternary Ammonium Methocarbonate or Quaternary Ammonium Alkylcarbonate to the Corresponding Quaternary Ammonium Bicarbonate The quaternary ammonium methocarbonate or alkylcarbonate produced by the method of the present invention can be converted to a corresponding bicarbonate, carbonate, or mixture thereof by methods known in the art, such as hydrolysis and other exchange reactions (e.g., de-hydrolysis). For example, the methocarbonate or alkylcarbonate may be stirred with water at ambient conditions to effect the reaction (hydrolysis) to the corresponding bicarbonate and an alkanol (methanol in the case of the methocarbonate and $R^9OH$, $R^{10}OH$, or a mixture thereof in the case of the alkylcarbonate). Water may then be added to distill out the water and any residual methanol or methanol or other alkanol formed when the methocarbonate or alkylcarbonate hydrolyzes to the bicarbonate. The distillation may be done at atmospheric or reduced pressures by methods standard in the art.

The bicarbonate can be converted to the carbonate by any method in the art. For instance, the bicarbonate can be heated (e.g. in water) to yield the corresponding carbonate, carbon dioxide, and water.

If methanol is distilled out of the bicarbonate solution, the heat may cause some or all of the bicarbonate to be converted to the corresponding carbonate.

The methanol and alkanol in the product can be recovered by any method known in the art, such as distillation as discussed above, during or after the reaction. The quaternary ammonium bicarbonate may be isolated and purified by methods known in the art.

The method of the present invention can produce quaternary ammonium bicarbonates having the formula

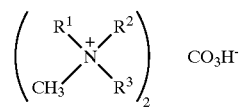

and quaternary ammonium carbonates having the formula

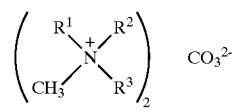

wherein $R^1$, $R^2$, and $R^3$ are defined as above.

According to a preferred embodiment, the conversion results in the formation of a mixture containing from about 70 to about 90% by weight of quaternary ammonium bicarbonate and from about 10 to about 30% by weight of quaternary ammonium carbonate, based upon 100% total weight of quaternary ammonium bicarbonate and quaternary ammonium carbonate.

Mixing, adding, and reacting steps in the present invention can be accomplished by conventional means known to those of ordinary skill in the art. The order of addition of reactants or solvent in any individual step does not affect the process. Reactants and/or solvent can be added sequentially or simultaneously in any suitable reaction vessel. Importantly, the method of the present invention is suitable for commercial scale production techniques and equipment, yet convenient for small scale work.

The following examples illustrate the invention without limitation. All parts and percentages are given by weight unless otherwise indicated.

A. Measurement of the Conversion of an Amine to the Corresponding Quaternary Ammonium Methocarbonate The amount of amine converted to the corresponding quaternary ammonium methocarbonate was determined as follows. Gas chromatography was performed on a given sample after formation of the quaternary ammonium methocarbonate. Gas chromatography measurements of the solution were performed with a Hewlett Packard Model 5890 Series II chromatograph equipped with a Hewlett Packard 7673 GC/SFC auto-injector which injects 1 μl of solution into the injector at 300° C. The column temperature starts at 100° C. with a 5 minute hold followed by ramping at 8° C. per minute to 300° C., followed by another 5 minute hold.

In the gas chromatography injector, the quaternary ammonium methocarbonate decomposes. For example, didecyldimethyl ammonium methocarbonate decomposes to produce predominantly decene and decyldimethylamine and small amounts of didecylmethylamine. In a pure solution of didecyldimethyl ammonium methocarbonate, the didecylmethylamine peak contributes 13% of the areas of the total chromatogram. The percentage of didecylmethylamine and propylene carbonate converted to didecyldimethyl ammonium methocarbonate was calculated by following the decrease in area for the didecylmethylamine peak from 100% initially to 13% representing 100% conversion. The amount of other amines converted can be determined by similar methods.

A two phase titration with a standard sodium lauryl sulfate titrant and bromophenol blue indicator was performed to confirm the formation of quaternary ammonium compounds.

B. Preparation of Quaternary Ammonium Methocarbonate

The following examples were performed in a 1 liter stainless steel Parr Model 4520 reactor equipped with a magnetic stirrer and a turbine type impeller. The temperature of the reactor was controlled to within ±1° C. by a Parr Model 4843 controller with an electrical external heater and internal cooling by a water filled coil. An Ashcroft pressure gauge capable of measuring pressures ranging from 0 to 200 psi was attached to the reactor. A small bleed valve was kept partially open until the contents of the reactor reached 60° C. to facilitate removal of residual air in the reactor.

EXAMPLE 1

The reactor was charged with 295 g (0.95 moles) didecylmethylamine (92% (w/w) pure and 8% (w/w) tridecylamine), 153 g (1.5 moles) propylene carbonate, and 177 g (5.7 moles) of methanol. The mixture was heated to 140° C. with stirring for 28 hours. Didecyldimethyl ammonium methocarbonate was produced.

Initially, the solution consisted of two phases. The top layer was essentially pure didecylmethyl amine. After 15 hours, the solution was a single phase. When a sample of the solution after 15 hours of heating was allowed to cool to room temperature, it became hazy and separated into two phases.

According to gas chromatography, about 90 to 95% of the didecylmethylamine was converted to didecyldimethyl ammonium methocarbonate after 15 hours of heating and about 99% of the didecylmethylamine was converted to didecyldimethyl ammonium methocarbonate after 28 hours of heating.

EXAMPLE 2

The reactor was charged with didecylmethylamine, propylene carbonate, and methanol at a molar ratio of 1:1.2:6.5. The mixture was heated to 130° C. for 16 hours. Didecyldimethyl ammonium methocarbonate was produced. Initially, the solution consisted of two phases. After heating, the solution remained in two phases. The top layer was high in tridecylamine.

According to gas chromatography, about 75–80% of the didecylmethylamine was converted to didecyldimethyl ammonium methocarbonate after the 16 hours of heating.

EXAMPLE 3

A reactor was charged with didecylmethylamine, propylene carbonate, and methanol at a molar ratio of 1:1.6:10. The mixture was heated to 130° C. for 20 hours. Didecyldimethyl ammonium methocarbonate was produced. Initially, the solution consisted of two phases. After 16 hours of heating, the solution consisted of one phase.

According to gas chromatography, about 85–90% of the didecylmethylamine was converted to didecyldimethyl ammonium methocarbonate after the 20 hours of heating.

EXAMPLE 4

The reactor was charged with didecylmethylamine (100% pure), propylene carbonate, and methanol at a molar ratio of 1:2:10. The mixture was heated to 140° C. for 23 hours. Didecyldimethyl ammonium methocarbonate was produced. Initially, the solution consisted of two phases. After 6 hours of heating, the solution consisted of one phase.

According to gas chromatography, about 97–100% of the didecylmethylamine was converted to didecyldimethyl ammonium methocarbonate after the 23 hours of heating.

EXAMPLE 5

The reactor was charged with 233 g (0.75 moles) didecylmethylamine (96% (w/w) pure and 4% (w/w) tridecylamine), 76.5 g (0.75 moles) propylene carbonate, 67.5 g (0.75 moles) dimethyl carbonate, and 233 g (7.5 moles) methanol. The mixture was heated to 140° C. for 8.5 hours. Didecyl-dimethyl ammonium methocarbonate was produced. Initially, the solution consisted of two phases. After 2.5 hours, the solution consisted of one phase.

According to gas chromatography, about 75, 95, and 99% of the didecylmethylamine was converted to didecyldimethyl ammonium methocarbonate after 2.5, 5.5, and 8.5 hours of heating.

EXAMPLE 6

The reactor was charged with didecylmethylamine, propylene carbonate, methanol, and dimethyl carbonate at a molar ratio of 1:1:4:0.4. The mixture was heated to 150° C. for 20 hours. Didecyldimethyl ammonium methocarbonate was produced. Initially, the solution consisted of two phases. After the 20 hours of heating, the solution consisted of two phases.

According to gas chromatography, about 75% of the didecylmethylamine was converted to didecyldimethyl ammonium methocarbonate after the 20 hours of heating.

EXAMPLE 7

The reactor was charged with didecylmethylamine, propylene carbonate, methanol, and dimethyl carbonate at a molar ratio of 1:1:10:1. The mixture was heated to 130° C. for 21 hours. Didecyldimethyl ammonium methocarbonate was produced. Initially, the solution consisted of two phases. After the 21 hours of heating, the solution consisted of one phase.

According to gas chromatography, about 97% of the didecylmethylamine was converted to didecyldimethyl ammonium methocarbonate after the 21 hours of heating.

EXAMPLE 8

The reactor was charged with didecylmethylamine, propylene carbonate, methanol, and dimethyl carbonate at a molar ratio of 1:1:7:0.7. The mixture was heated to 140° C. for 15 hours. Didecyldimethyl ammonium methocarbonate was produced. Initially, the solution consisted of two phases. After 6 hours of heating, the solution consisted of one phase.

According to gas chromatography, about 98% of the didecylmethylamine was converted to didecyldimethyl ammonium methocarbonate after the 15 hours of heating.

EXAMPLE 9

The reactor was charged with didecylmethylamine, propylene carbonate, methanol, and dimethyl carbonate at a molar ratio of 1:1:4:1. The mixture was heated to 150° C. for 17 hours. Didecyldimethyl ammonium methocarbonate was produced. Initially, the solution consisted of two phases. After the 17 hours of heating, the solution consisted of one phase.

According to gas chromatography, about 85% of the didecylmethylamine was converted to didecyldimethyl ammonium methocarbonate after 17 hours of heating.

EXAMPLE 10

The reactor was charged with didecylmethylamine, propylene carbonate, methanol, and dimethyl carbonate at a molar ratio of 1:1:7:0.7. The mixture was heated to 150° C. for 16 hours. Didecyldimethyl ammonium methocarbonate was produced. Initially, the solution consisted of two phases. After 3 hours of heating, the solution consisted of one phase.

According to gas chromatography, about 98% of the didecylmethylamine was converted to didecyldimethyl ammonium methocarbonate after the 16 hours of heating.

EXAMPLE 11

The reactor was charged with didecylmethylamine, propylene carbonate, methanol, and dimethyl carbonate at a molar ratio of 1:1:10:1. The mixture was heated to 120° C. for 28 hours. Didecyldimethyl ammonium methocarbonate was produced. Initially, the solution consisted of two phases. After 10 hours of heating, the solution consisted of one phase.

According to gas chromatography, about 98–100% of the didecylmethylamine was converted to didecyldimethyl ammonium methocarbonate after the 28 hours of heating.

EXAMPLE 12

The reactor was charged with didecylmethylamine, propylene carbonate, methanol, and dimethyl carbonate at a molar ratio of 1:1:10:1. The mixture was heated to 140° C. for 15 hours. Didecyldimethyl ammonium methocarbonate was produced.

According to gas chromatography, 95–98% of the didecylmethylamine was converted to didecyldimethyl ammonium methocarbonate after the 15 hours of heating.

EXAMPLE 13

The reactor was charged with dodecyldimethylamine, propylene carbonate, and methanol at a molar ratio of 1:2:10. The mixture was heated to 140° C. for 6 hours. Dodecyltrimethyl ammonium methocarbonate was produced.

According to gas chromatography, 96% and 100% of the dodecyldimethylamine, respectively, was converted to dodecyltrimethyl ammonium methocarbonate after 3 and 6 hours of heating.

EXAMPLE 14

The reactor was charged with dodecyldimethylamine, propylene carbonate, dimethyl carbonate, and methanol at a molar ratio of 1:1:1:10. The mixture was heated to 140° C. for 3 hours. Dodecyltrimethyl ammonium methocarbonate was produced.

According to gas chromatography, 100% of the dodecyldimethylamine was converted to dodecyltrimethyl ammonium methocarbonate after the 3 hours of heating.

EXAMPLE 15

The reactor was charged with dioctylmethylamine, propylene carbonate, and methanol at a molar ratio of 1:2:10. The mixture was heated to 140° C. for 14 hours. Dioctyldimethyl ammonium methocarbonate was produced. Initially, the solution consisted of two phases. After 5.5 hours of heating, the solution consisted of one phase.

According to gas chromatography, 85% and 98% of the dioctylmethylamine, respectively, was converted to dioctyldimethyl ammonium methocarbonate after 5.5 and 14 hours of heating.

EXAMPLE 16

The reactor was charged with octadecyldimethylamine, propylene carbonate, and methanol at a molar ratio of 1:2:10. The mixture was heated to 140° C. for 5 hours. Octadecyltrimethyl ammonium methocarbonate was produced.

According to gas chromatography, 97% of the octadecyldimethylamine was converted to octadecyltrimethyl ammonium methocarbonate after the 5 hours of heating.

EXAMPLE 17

The reactor was charged with dioctadecylmethylamine, propylene carbonate, and methanol at a molar ratio of 1:2:10. The mixture was heated to 140° C. for 26 hours. Dioctadecyldimethyl ammonium methocarbonate was produced.

According to gas chromatography, 80% of the dioctadecylmethylamine was converted to dioctadecyldimethyl ammonium methocarbonate.

EXAMPLE 18

The reactor was charged with trioctylamine, propylene carbonate, and methanol at a molar ratio of 1:2:10. The mixture was heated to 140° C. for 38 hours. Trioctylmethyl ammonium methocarbonate was produced. Initially, the solution consisted of two phases. After 38 hours of heating, the solution still consisted of two phase.

According to gas chromatography, 85% of the trioctylamine was converted to trioctylmethyl ammonium methocarbonate after the 38 hours of heating.

EXAMPLE 19

The reactor was charged with didecylmethylamine, ethylene carbonate, and methanol at a molar ratio of 1:2:10. The mixture was heated to 140° C. for 26 hours. Didecyldimethyl ammonium methocarbonate was produced. Initially, the solution consisted of two phases. After 6 hours of heating, the solution consisted of one phase. Furthermore, after 26 hours the solution was dark.

According to gas chromatography, 85% of the didecylmethylamine was converted to didecyldimethyl ammonium methocarbonate after the 26 hours of heating.

C. Preparation of Quaternary Ammonium Bicarbonate

EXAMPLE 20

The mixture from Example 1 was cooled and transferred to a round bottom flask equipped with a Vigreux column having a distillation head condenser receiving flask cooled in a dry ice acetone bath and a connection to a vacuum system. The flask was placed in an oil bath and heated slowly as the vacuum was dropped to 0.2 atm. Distillation continued over a 3 hour period as the bath temperature was slowly raised to 75° C. A total of 165 grams of liquid was collected. Using a density curve based on known mixtures of dimethyl carbonate (density 1.07 g/cc) and methanol (density 0.79 g/cc), it was estimated that the mixture from Example 1 contained 20% by weight of dimethyl carbonate.

400 grams of water were added to the flask and the flask was placed in the oil bath. The vacuum was slowly applied to distill out water (about 250 grams total) at a temperature of 55–75° C. over a period of about 5 hours until a sample of the distillate had a density of greater than 0.98 g/cc. The product contained about 600 grams of combined quaternary ammonium bicarbonate and carbonate (60%), propylene glycol and water and less than 1% methanol. An additional 110 grams of water was added to dilute the mixture to yield a product containing 50% by weight of combined quaternary ammonium bicarbonate and carbonate, 16% by weight of propylene glycol, and 34% by weight of water.

EXAMPLE 21

The methocarbonate in the mixture obtained in Example 7 was converted to the corresponding bicarbonate and carbonate by the procedure described in Example 20. The resulting mixture contained 50% by weight of combined quaternary ammonium bicarbonate and carbonate, 10% by weight of propylene glycol, and 40% by weight of water.

EXAMPLE 22

A 50 gallon reactor, equipped with a stripping condenser and a 30 gallon receiver, was charged with 116.4 lbs (0.374 lb moles) of didecylmethyl amine, 38.2 lbs (0.374 lb moles) of propylene crabonate, 33.7 lbs (0.374 lb moles) of dimethyl carbonate, and 119.7 g (3.740 lb moles) of methanol. The reactor was heated to and maintained at 140° C. for 6–9 hours. The reactor was maintained at 150 psig. After 6 hours at 140° C., the reactor was sampled to determine the percentage of quaternary ammonium compound and free amine in the reactor. The reaction mixture was periodically sampled until the ratio of quaternary ammonium compound to unreacted amine was greater than 97.5:2.5. The quaternary ammonium compound was identified by NMR as didecyldimethylammonium methocarbonate.

Excess methanol and dimethyl carbonate was removed by atmospheric stripping at 100° C. until no more distillate was collected. The reactor was cooled to 60° C. The content of the stripping condenser and receiver was drained into a 55 gallon drum. Full glycol cooling was applied to the stripping condenser and receiver and full vacuum (~4 mm Hg) was applied to the reactor system to further strip off any remaining dimethylcarbonate and methanol. When no more distillate was collected, the reactor was vented with nitrogen to atmospheric pressure. The content of the receiver was drained into the 55 gallon drum. A total of 129 lbs of dimethylcarbonate and methanol was collected in the drum.

To the content of the reactor at 60° C. was added 109.6 lbs of water. The reactor was heated and maintained at 80° C. for 2–3 hours. The didecyldimethylammonium methocarbonate was hydrolyzed to didecyldimethylammonium bicarbonate/carbonate. Additional water was added so that the final concentration of the quaternary ammonium compound was about 50–52%, the propylene glycol was about 9–11%, and methanol was less than 3.5%.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A method of preparing a quaternary ammonium alkylcarbonate having the formula

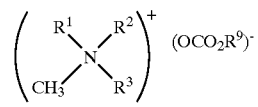

wherein $R^1$ and $R^2$ are independently $C_1$–$C_{30}$ alkyl, $R^3$ is a $C_8$–$C_{30}$ alkyl, and $R^9$ is a $C_1$–$C_{10}$ alkyl, the method comprising reacting (a) an amine having the formula $NR^1R^2R^3$;

(b) an ester having the formula

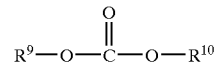

wherein $R^{10}$ is a $C_1$–$C_{10}$ alkyl; and (c) methanol to form the quaternary ammonium alkylcarbonate.

2. The method of claim 1, wherein $R^1$ is methyl and $R^2$ and $R^3$ are independently $C_8$–$C_{12}$ alkyl.

3. The method of claim 1, wherein the amine is selected from the group consisting of didecylmethylamine, dodecyldimethylamine, dioctylmethylamine, octadecyldimethylamine, dioctadecylmethylamine, trioctylamine, and any combination of any of the foregoing.

4. The method of claim 1, wherein the molar ratio of amine to ester ranges from about 1:1 to about 1:10.

5. The method of claim 4, wherein the molar ratio of amine to ester ranges from about 1:2 to about 1:3.

6. The method of claim 1, wherein the molar ratio of amine to methanol ranges from about 1:2 to about 1:20.

7. The method of claim 1, wherein the reaction step is performed at from about 120 to about 160° C.

8. The method of claim 7, wherein the reaction step is performed at from about 120 to about 150° C.

9. The method of claim 8, wherein the reaction step is performed at from about 120 to about 140° C.

10. The method of claim 1, further comprising the step of recovering alkanol having the formula $R^9OH$.

11. The method of claim 1, wherein the reaction step comprises reacting (a) the amine;

(b) the ester;

(c) methanol; and (d) alkyl methyl carbonate having the formula $CH_3OC(O)OR^9$.

12. A method of preparing a quaternary ammonium bicarbonate having the formula

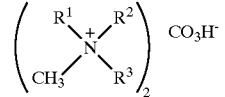

wherein $R^1$, $R^2$, and $R^3$ are independently $C_1$–$C_{30}$ alkyl, the method comprising (a) preparing a quaternary ammonium alkylcarbonate by the method of claim 1; and (b) converting the quaternary ammonium alkylcarbonate to the quaternary ammonium bicarbonate.

* * * * *